United States Patent [19]
Maytal

US005702435A

[11] Patent Number: 5,702,435
[45] Date of Patent: *Dec. 30, 1997

[54] FAST CHANGING HEATING-COOLING DEVICE AND METHOD

[75] Inventor: Ben-Zion Maytal, Atlit, Israel

[73] Assignee: State Of Israel Ministry Of Defense, Rafael-Armaments, Israel

[*] Notice: The term of this patent shall not extend beyond the expiration date of Pat. No. 5,522,870.

[21] Appl. No.: 599,630

[22] Filed: Feb. 9, 1996

Related U.S. Application Data

[63] Continuation of Ser. No. 178,510, Jan. 7, 1994, Pat. No. 5,522,870.

[30] Foreign Application Priority Data

Jan. 25, 1993 [IL] Israel .................................. 104506

[51] Int. Cl.$^6$ ............................................ A61F 7/00
[52] U.S. Cl. ............................................ 607/104
[58] Field of Search .................... 606/22–26, 21; 607/104–105, 107–112, 114

[56] References Cited

U.S. PATENT DOCUMENTS

| | | |
|---|---|---|
| 3,388,128 | 6/1968 | Day et al. . |
| 3,398,738 | 8/1968 | Lamb et al. . |
| 3,477,434 | 11/1969 | Hood, Jr. et al. . |
| 3,696,813 | 10/1972 | Wallach . |
| 3,782,386 | 1/1974 | Barger et al. . |
| 3,823,575 | 7/1974 | Parel . |
| 3,924,628 | 12/1975 | Droegemueller et al. . |
| 3,993,075 | 11/1976 | Lisenbee et al. . |
| 4,126,017 | 11/1978 | Bytniewski et al. . |
| 4,587,959 | 5/1986 | Ruderian . |
| 4,946,460 | 8/1990 | Merry et al. . |
| 5,078,713 | 1/1992 | Varney ............................ 606/23 |
| 5,139,496 | 8/1992 | Hed . |
| 5,147,355 | 9/1992 | Friedman et al. . |
| 5,254,116 | 10/1993 | Baust et al. ................... 607/105 X |
| 5,275,595 | 1/1994 | Dobak, III ....................... 606/23 |
| 5,365,750 | 11/1994 | Greenthal . |
| 5,522,870 | 6/1996 | Ben-Zion ........................ 607/104 |

FOREIGN PATENT DOCUMENTS

| | | |
|---|---|---|
| 0380217 | 8/1990 | European Pat. Off. . |
| 0447861 | 9/1991 | European Pat. Off. . |
| 0608927 | 8/1994 | European Pat. Off. . |
| 2207730 | 6/1974 | France . |
| 2242062 | 3/1975 | France . |
| 2368264 | 5/1978 | France . |
| 2399828 | 3/1979 | France . |
| 2477406 | 9/1981 | France . |

(List continued on next page.)

OTHER PUBLICATIONS

Andrew A. Gage, "Current Issues in Cryosurgery", *Cryobiology*, vol. 19, 1982, pp. 219–222.

Primary Examiner—Jennifer Bahr
Assistant Examiner—Ryan Carter
Attorney, Agent, or Firm—Merchant, Gould Smith, Edell Welter & Schmidt, P.A.

[57] ABSTRACT

A method for creating a surface having a fast changing temperature, comprises providing a heat exchanger coupled to an orifice opening into a jacket which is in contact with the surface to be heated and cooled, the said jacket forming a reservoir capable of housing a fluid in contact with the surface to be heated and cooled, and providing two gas sources, each gas source being independently connected to the said heat exchanger, one source providing a first gas, which liquefies when it expands through the said orifice, and the other gas source providing a second gas, having an inversion temperature lower than the temperature obtained by the liquefaction of the first gas, and causing the exhaust gas flowing out from the said jacket, to flow through the said heat-exchanger to preheat or precool the inflowing gas, as the case may be, and further causing the said first and the said second gas alternately to flow through the said heat exchanger and orifice, to cool or to heat the said surface; means being provided for allowing and stopping the flow of each gas through the said orifice.

36 Claims, 7 Drawing Sheets

FOREIGN PATENT DOCUMENTS

| | | |
|---|---|---|
| 2482445 | 11/1981 | France . |
| 26 38 206 | 3/1977 | Germany . |
| 33 43 664 | 3/1985 | Germany . |
| 37 16 746 | 12/1988 | Germany . |
| 0 774 549 | 10/1980 | U.S.S.R. . |
| 1 217 377 | 3/1986 | U.S.S.R. . |
| 1422445 | 1/1976 | United Kingdom . |
| 90/08144 | 7/1990 | WIPO . |
| 93/08752 | 5/1993 | WIPO . |
| 93/18714 | 9/1993 | WIPO . |

FAST CHANGING HEATING-COOLING DEVICE AND METHOD

This is a Continuation application of application Ser. No. 08/178,510, filed Jan. 7, 1994, now U.S. Pat. No. 5,522,870 which application is incorporated herein by reference.

FIELD OF THE INVENTION

The present invention relates to a method and apparatus for obtaining fast changes in the temperature of a variable temperature element, and to the use of such method and apparatus. More particularly, the invention is directed to a method and apparatus which permit to cool a given area in the cryogenic range, and to heat the same area to relatively high temperatures, within very short periods of time, and vice versa.

BACKGROUND OF THE INVENTION

The ability to cause fast changes in temperatures, particularly between very low temperatures and room or higher temperatures, on a desired surface and at a desired location, is of practical importance in many uses. Fast temperature changes can be exploited, for instance, in the treatment of various materials, for sealing or surface curing purposes, etc.

Cold and hot surfaces are used also for medical uses. For instance, cryogenic techniques are employed to destroy malignant tissues, or for plastic surgery. One example of such a use is presented in SU 774,549, which relates to a thermal treatment of biological tissues by passing heat carriers through a cryosurgical probe. The method is said to be useful in the cryo-surgery of the human brain. This method, however, involves passing a heat carrier through a surgical probe, its subsequent heating and repeated passage through the probe. Acetone or alcohol are used as the heat carrier. Prior to its passage through the probe the heat carrier is either cooled to $-70°-75°$ C., or heated to $+70°-90°$ C.

Devices of this type present severe drawbacks, inasmuch as they have long lags in temperature changes, they require cumbersome heating/cooling apparatus outside the probe, and are complicated and expensive to use.

Cryosurgical instruments having both crycooling and heating capabilities are also known in the art. One such device and its medical use have been described by Andrew A. Gage ["Current Issues in Cryosurgery", *Cryobiology* 19, 219–222(1982), at pp. 220–21]. The device described therein was cooled by liquid nitrogen and electrically heated, to provide hemostasis. The electrical heating, however, by its nature is a relatively slow procedure.

Another device is described in SU 1,217,377, which exploits the expansion of gases through an orifice. However, simple expansion of gas through an orifice provides relatively slow temperature changes, and the changes in temperature are relatively mild. Thus, for instance, in the device of SU 1,217,377 it is not possible to liquify nitrogen. Additionally, this prior art device employs helium at room temperature which, expanding from a pressure of about 300 atmospheres, will attain a heating of merely about 30° C. In any case, in the single pass expansion described in this reference, liquefaction of nitrogen cannot be achieved. However, helium has an inversion temperature of about 45K, which renders it possible to employ neon or hydrogen as the second gas, as is done in this reference. The highest inversion temperature of neon is about 200K, and of hydrogen is about 180K. Accordingly, these gases cannot be used while using nitrogen as the first gas, because the temperature of liquid nitrogen is 80K, and thus the heating obtainable with neon and hydrogen is low. Additionally, neon and hydrogen may be found at an inversion temperature lower than their maximal temperature, so that no heating is obtained. However, neon is expensive and hydrogen is dangerous, and the obtainable temperatures are unsatisfactory for many uses, which accounts for the lack of success of the above-mentioned device.

Prior art devices and methods have so far failed to provide simple and effective fast temperature changing means which can be used in order to exploit the potential of cryogenic techniques, in industry and in medicine. It is therefore clear that it would be highly desirable to be able to exploit such methods in as many as possible applications.

SUMMARY OF THE INVENTION

It is an object of the present invention to provide a method by means of which a fast and periodic change of surface temperature, even down to cryogenic range, can be created, at the desired location, in a simple and effective manner.

It is another object of the invention to provide a device exploiting the method (hereinafter referred to as "probe", for the sake of brevity), which is simple and inexpensive in construction and in operation, and which overcomes the drawbacks of prior art devices.

Other objectives of the invention will become apparent as the description proceeds.

The method for creating a surface having a fast changing temperature, according to the invention, comprises providing a heat exchanger coupled to an orifice opening into a jacket which is in contact with the surface to be heated and cooled, the said jacket forming a reservoir capable of housing a fluid in contact with the surface to be heated and cooled, and providing two gas sources, each gas source being independently connected to the said heat exchanger, one source providing a first gas, which liquefies when it expands through the said orifice, and the other gas source providing a second gas, having an inversion temperature lower than the temperature obtained by the liquefaction of the first gas, and causing the exhaust gas flowing out from the said jacket, to flow through the said heat-exchanger to preheat or precool the inflowing gas, as the case may be, and further causing the said first and the said second gas alternately to flow through the said heat exchanger and orifice, to cool or to heat the said surface; means being provided for showing and stopping the flow of each gas through the said orifice.

The selection of appropriate gases to be used according to the invention is crucial. For instance, the maximum inversion temperature of helium is 43K. Thus, even when somewhat precooled by boiling nitrogen at 77.3K, it still will warm up when undergoing Joule-Thomson expansion. Furthermore, providing a preheating or precooling of the inflowing gas is not just a matter of efficiency or saving, but is an essential part of the invention, since processes and devices employing a one-pass heating or cooling, without utilizing an exchange of heat via an appropriate heat-exchanger, will not provide sufficiently low or sufficiently high temperatures, and will result in a temperature change which is excessively slow. As stated, the fast change from one extreme temperature to the other is an essential feature of the invention.

Heat exchangers can be of any type, and may be, e.g., a finned tube heat-exchanger of a porous-matrix heat-exchanger, e.g., of the type described in British Patent No. 1,422,445. The device described in this British patent provides only for the cryocooling of the probe, the purpose being to maintain the temperature of the probe below −80° C., thus avoiding altogether the need for heating the probe. It should be mentioned that, according to the teachings of this patent, heating was necessary, when operating at temperatures above −80° C., for the purpose to prevent the probe from sticking to the tissue. However, when operating according to the invention, with fast cooling-heating cycles, the heat exchanger can be utilized also for heating purposes.

In one preferred embodiment of the invention, the fast change in temperature is periodic. In another preferred embodiment of the invention the fast change is controlled and effected at the time selected by the operator.

According to a preferred embodiment of the invention, the first gas is selected from the group consisting essentially of argon, nitrogen, air, krypton, $CF_4$, xenon and $N_2O$, and the second gas is helium.

Cryogenic liquefaction occurs at the tip of the cold extremity of the device operating according to the invention as will be more fully explained hereinafter, under the cooled metal surface. The Linde-Hampson method is applied, using the Joule-Thomson effect for cooldown to liquefaction.

The invention also encompasses an apparatus for the cryocooling and the heating of surfaces, comprising:

1) a heat exchanger coupled to an orifice, the said orifice opening into a jacket;

2) a jacket which is in contact with the surface to be heated and cooled, the said jacket forming a reservoir capable of housing a fluid in contact with the surface to be heated and cooled;

3) two pressurized gas sources, each gas source being independently connected to the said heat exchanger;

4) means for allowing and stopping the flow of each gas through the said orifice.

According to one embodiment of the invention, the pressurized gas sources are gas reservoirs containing gas under pressure. According to another embodiment of the invention, the gas sources comprise one or more compressors, which draw gas from a reservoir containing gas at a lower pressure than desired.

The surface which is heated and cooled may have any desired shape. According to one preferred embodiment there are provided changeable elements which are mounted on the jacket, having different shapes, according to the use which it is desired to make of the probe.

It should furthermore be understood that for some uses it is important to obtain a high frequency of temperature change, while it is less important to reach extreme temperatures. Thus, for instance, one may which, for a given application, to oscillate between temperatures of −50° C. and +100° C. only. As will be understood by the skilled person, limiting the upper and/or the lower limit of the desired temperature permits to oscillate between them much more quickly, and the invention also comprises providing such quick oscillations with non-extreme and non cryogenic temperatures. Of course, the skilled engineer will be able to select the appropriate gases to be used for a given application, depending on the temperatures which it is desired to use.

The invention is also directed to a method of selectively destroying a plurality of cells of a living organism, comprising bringing into contact with the surface where the cells to be destroyed are located, a probe according to the invention, and causing extreme temperature changes to take place at the contact surface thereof. It should be noted that, unlike the methods of the prior art in which heating was performed by electrical means, to obtain cauterization, or for avoiding the sticking of the probe to the cells, according to the invention the change in heating is an essential part of the method, and is this change which, apart from the advantages mentioned above, permits to control the depth of penetration of the cold front, and to provide the temperature shock to the cells.

According to a preferred embodiment of the invention, the treated surface is the epidermis. According to another preferred embodiment of the invention, the treated surface is the human brain or eye.

Also encompassed by the invention is a method for generating a fast cyclically change of temperature, said method comprising sequentially cooling/heating of a surface by alternate gas supply to a Joule-Thomson liquefaction device.

DETAILED DESCRIPTION OF PREFERRED EMBODIMENTS

Figure 1:
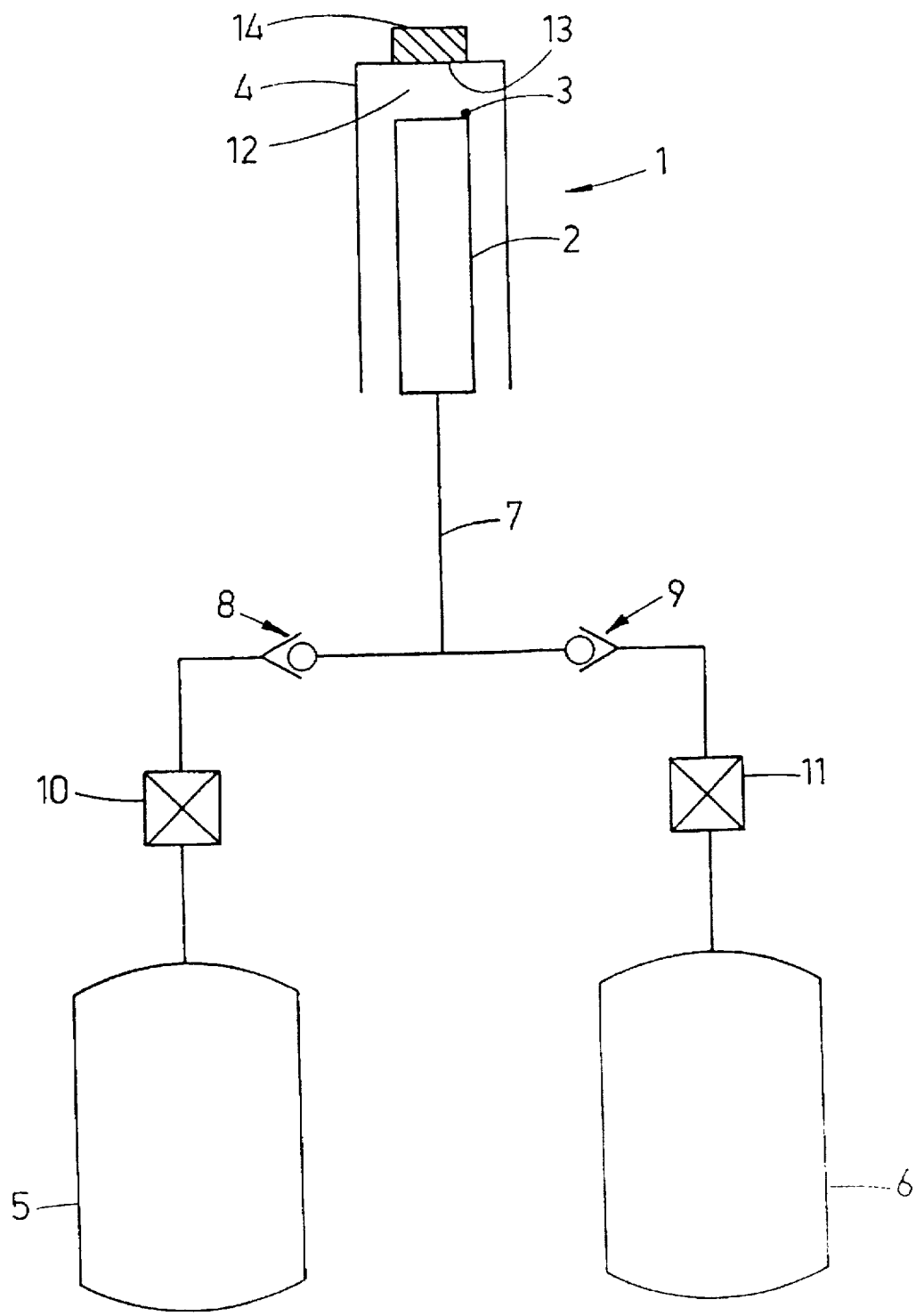
FIG. 1 is a schematic representation of an apparatus according to the invention, which is used to illustrate the method.

Looking now at FIG. 1, numeral 1 generally indicates a probe, comprising a heat-exchanger 2, an orifice, 3, and an isolated jacket 4, which together constitute a Joule-Thompson device. Two gas reservoirs, 5 and 6, containing gas under pressure of about 40 MPa are connected to the said heat-exchanger 2, via line 7, through one-way valves 8 and 9, and on-off valves 10 and 11. Alternatively, two compressors can be provided, to compress the gases of reservoirs 5 and 6.

When an on-off valve (10 or 11) is opened, gas flows through line 7 into heat exchanger 2, and exits orifice 3 to form a cryogen pool, indicated by numeral 12. Probe surface 13 is either cooled or heated by this pool, depending on the gas used at the time, and cools the surface of the object schematically indicated at 14, which is brought into contact with it.

Figure 2:
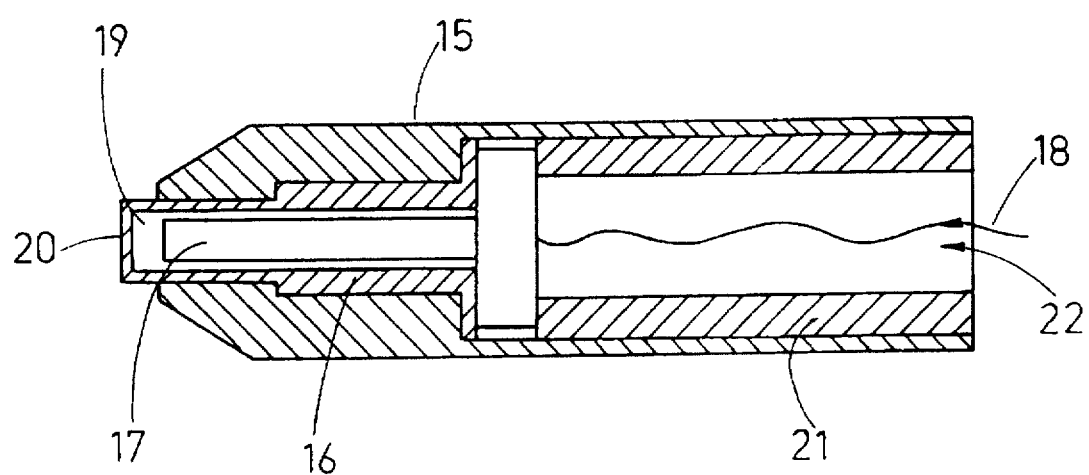
FIG. 2 is a detailed representation of a probe, according to one preferred embodiment of the invention, shown in cross-section.

The design of a probe, according to one embodiment of the invention, is more fully illustrated in FIG. 2. An isolating sleeve 15 houses the various parts of the probe, which include a steel encapsulation 16, containing a cryocooler 17. High pressure gas is supplied through a supply line 18, and expands through an orifice (not shown). The hot or cold gas creates a pool 19, which is in contact with the heating/cooling surface 20, which is the surface used to apply cold and heat to the treated body. An additional sleeve 21 is provided for holding the cryocooler 17 in place, and the exhaust gas leaves the probe through the empty space 22 therein.

Figure 5:
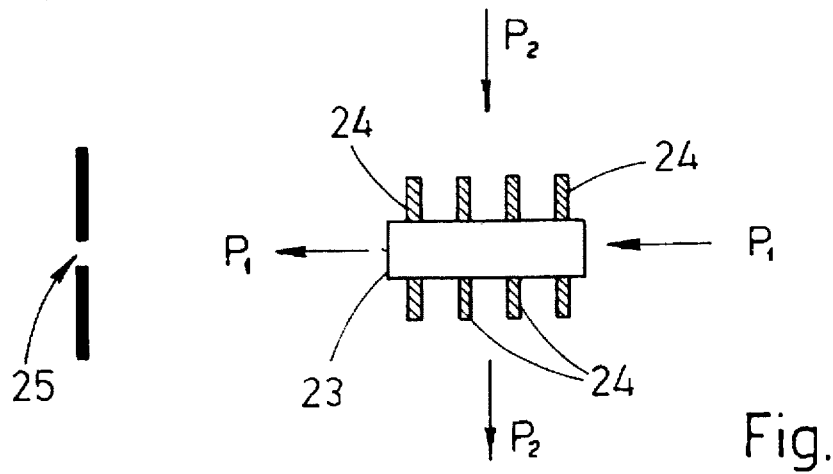
FIG. 5 schematically shows a portion of a finned tube.

FIG. 5 schematically shows a segment of a finned tube 23 of a heat exchanger used in connection with the invention. The fins 24 are distributed along the tube. Gas at a high pressure, P1, flows within tube 23, towards orifice 25,, while exhaust gas, at a lower pressure P2, flows across the tube, as shown by the arrows.

Figure 6:
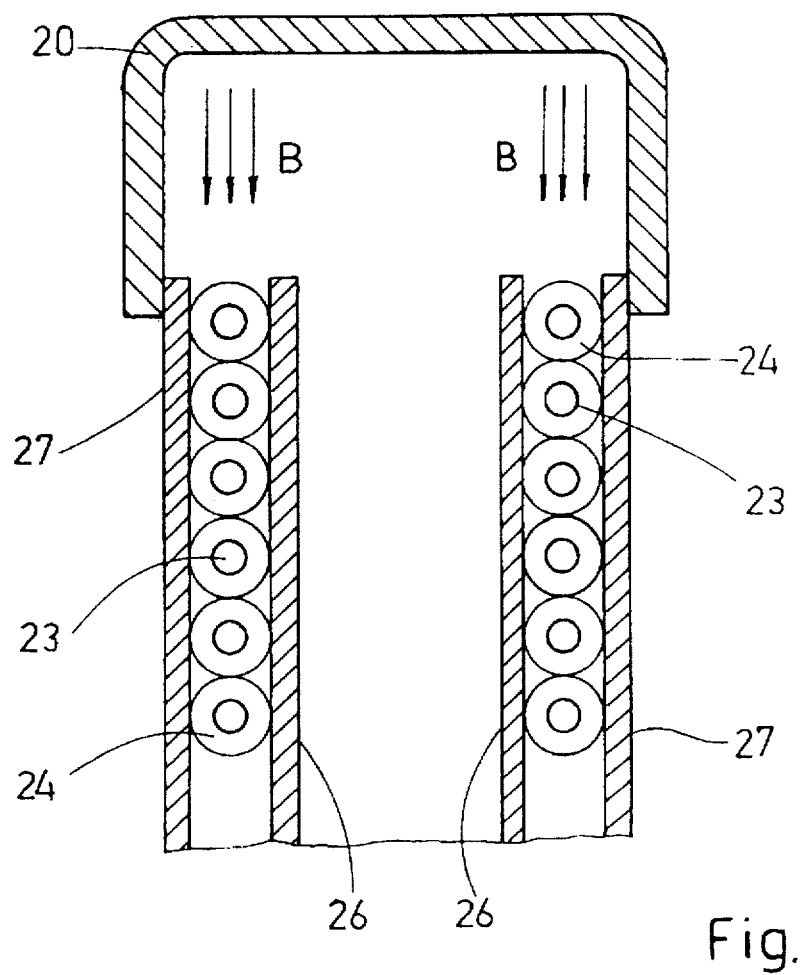
FIG. 6 is a schematic cross section of a device according to one preferred embodiment of the invention, the heat exchanger being shown.

In FIG. 6 the heat-exchanger is seen to be made of high pressure tubes 23, with fins 24, which are contained within an inner mandrel 26 and an outer mandrel 27. Gas backflowing from the cooled or heated surface 20, indicated by arrows B, flows into the heat-exchanger and comes into contact with the outer surface of the finned tube 23, thus exchanging heat with the gas flowing within it.

As stated, the invention can be exploited in a variety of medical uses. Some of the advantages obtained with the invention are:

a. Living cells destruction is more effective when operating with temperature cycles than when using cryogenic probes, as done according to the known art, which only cools the affected area.

b. Because temperature cycles are applied, the low temperature front does not penetrate too deep into healthy layers of the human body, in contrast to what happens when prior art cryogenic probes are used. Therefore, longer treatments of a superficial affected area are possible, according to the invention, while reducing the damage to healthy cells. In other words, the depth of cold front penetration is limited and controlled by the cycling frequency and, furthermore, it is independent of contact duration.

As will be appreciated by persons skilled in this art, by harmonic surface temperature profile, the depth of penetration obtained is proportional to $(\alpha \cdot \tau)^{1/2}$, $\alpha$ being the thermal diffusivity and $\tau$ the time period. This is known, e.g., from H. S. Carslaw and J. C. Jaeger, "Conduction of Heat in Solids", Chapter 2.6, Clavendon Press, Oxford, 1959.

c. At the end of the treatment cycle the probe can be heated to a temperature where there is no adhesion of the epidermis to the probe surface. Thus superficial damage is avoided, in contrast to what happens when attempting to remove a cool cryogenic probe from the skin.

Figure 7:
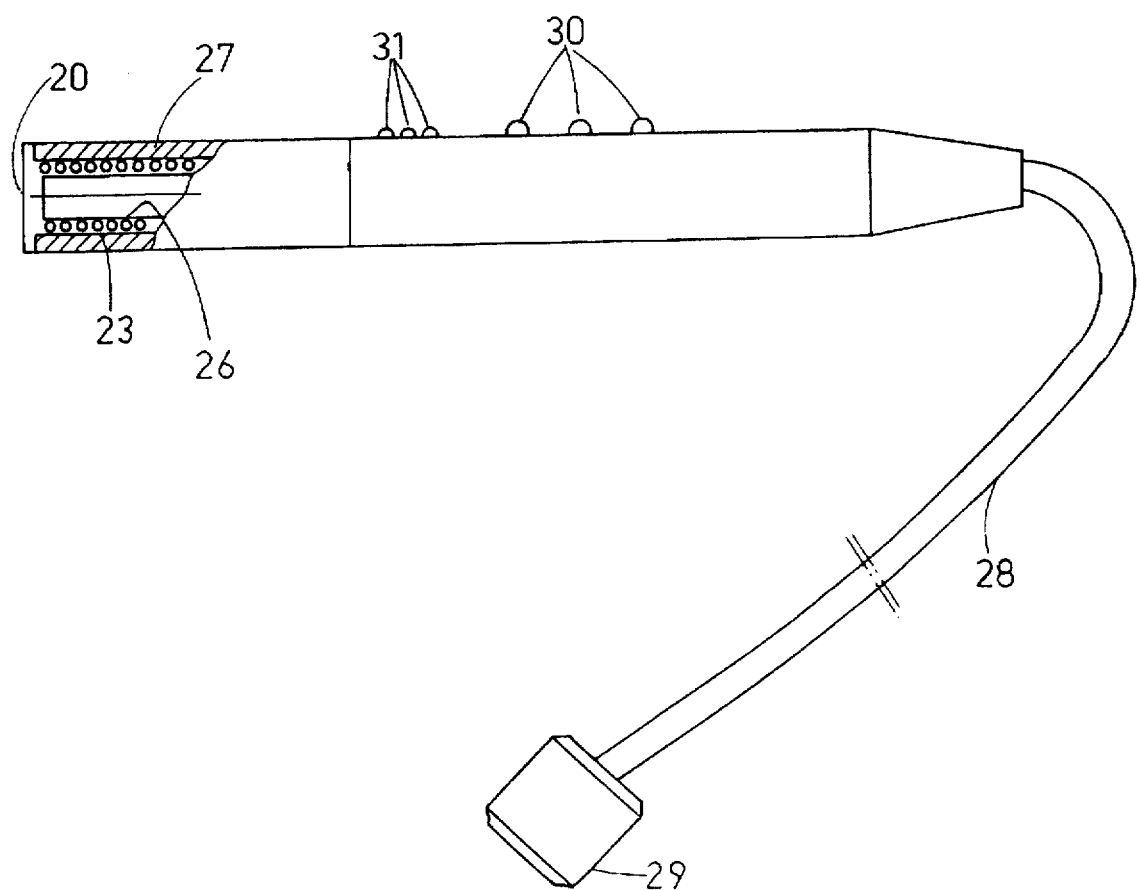
FIG. 7 schematically shows a probe according to one preferred embodiment of the invention.
Figure 8:
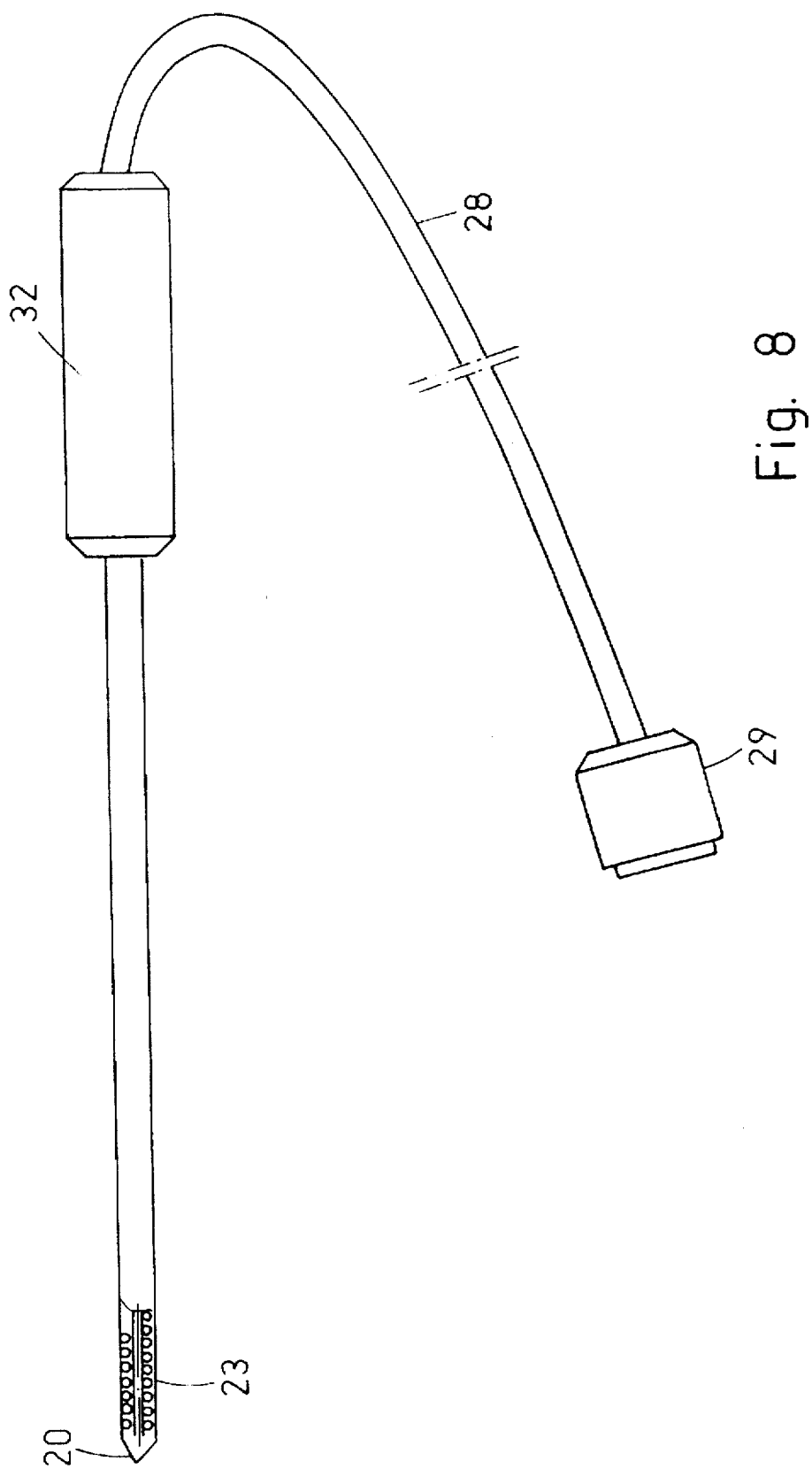
FIG. 8 schematically shows a probe according to another preferred embodiment of the invention.

As will be appreciated by the skilled person, probes according to the invention can be made of varying sizes for different uses, ranging from very thin probes to relatively large area probes, because the heating/cooling device can be accomodated even in very small volumes since no space-consuming parts are requires, such as electric heaters. Thus, for instance, FIG. 7 illustrates a flat, large area probe, such as may be suitable, e.g., for treatment of the epidermis or for non-medical applications. FIG. 8, on the other hand, shows a thin, pointed probe, such as may be used for penetration, e.g., into the liver for cancer therapy.

Looking at FIG. 7, and using the same numerals as in FIG. 6, for ease of understanding, the cooled and heated surface 20 is positioned near the heat-exchanger tubes 23, located between an inner mandrel 26 and an outer mandrel 27. Gas flows to the probe extremity through gas pipes located within outer sheat 28, which may contain two or more pipes, as well as electric wires, if desired. Pneumatic and electric connections can be effected, e.g., through connector 29 (the connections not being shown in detail). Flow of gases is controlled, according to this particular embodiment of the invention, through push-buttons or switches 30, positioned on the probe holder, so that the functioning of the probe is easily controlled by the user without having to shift the hand and without stopping the operation. Control lights 31 can also be provided, to indicate, e.g., when the heating or cooling gas is flowing, or when the operation of the probe has been altogether stopped.

Similarly, in FIG. 8 a thin probe is seen, in which the contact surface 20 is pointed and not flat. Because of the thinnes of the probe, the inner and outer mandrels are reduced in thickness, and are not shown for the sake of clarity. The probe holder 32, in this embodiment of the invention, can be located far from the pointed end of the probe, and can also be provided with buttons and indicating lights (not shown), as in FIG. 7.

Of course, many different shapes and sizes of probes can be provided, depending on the use for which they are intended, and the examples given above are only provided for the purpose of illustrating two of the possible different probes.

The invention will now be further illustrated through the following examples.

EXAMPLE 1

Heating-Cooling Cycles

The device described above was used in an experiment in which heating-cooling cycles were generated, and the temperature obtained at the surface (13) of the probe was recorded. The diameter of the heat-exchanger (2) was 5.2 mm, and it was kept under vacuum in excess of 100 Pa. The diameter of the orifice was 0.12 mm.

Helium at 10,000 psi (680 atm) was employed. Nitrogen was at 6000 psi and its flow rate was about 50 GLPM.

Figure 3:
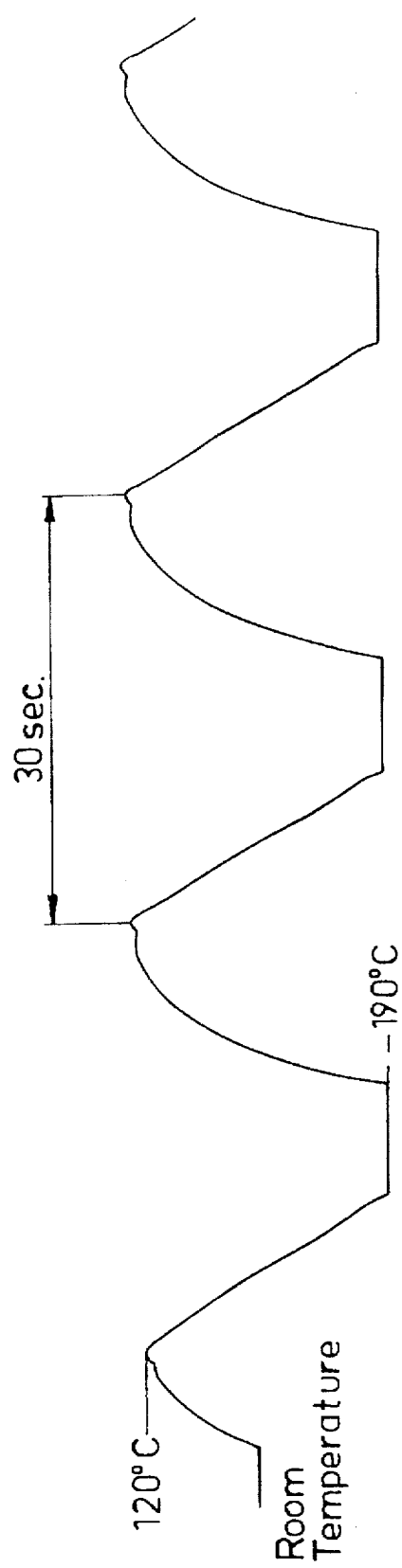
FIG. 3 shows the results of a heating/cooling experiment carried out with the probe of FIG. 2.

Heating was effected from room temperature, until a temperature of 120° C. was reached, after which the gas was changed and the probe was allowed to cool down to −190° C. The cooling and the heating times were almost the same, and the total cycle took about 30 seconds. This, as will be appreciated by the skilled person, is a surprisingly short time for such a cycle, which can hardly be obtained with prior art devices. The results are shown in FIG. 3.

EXAMPLE 2

Heating Experiment

Figure 4:
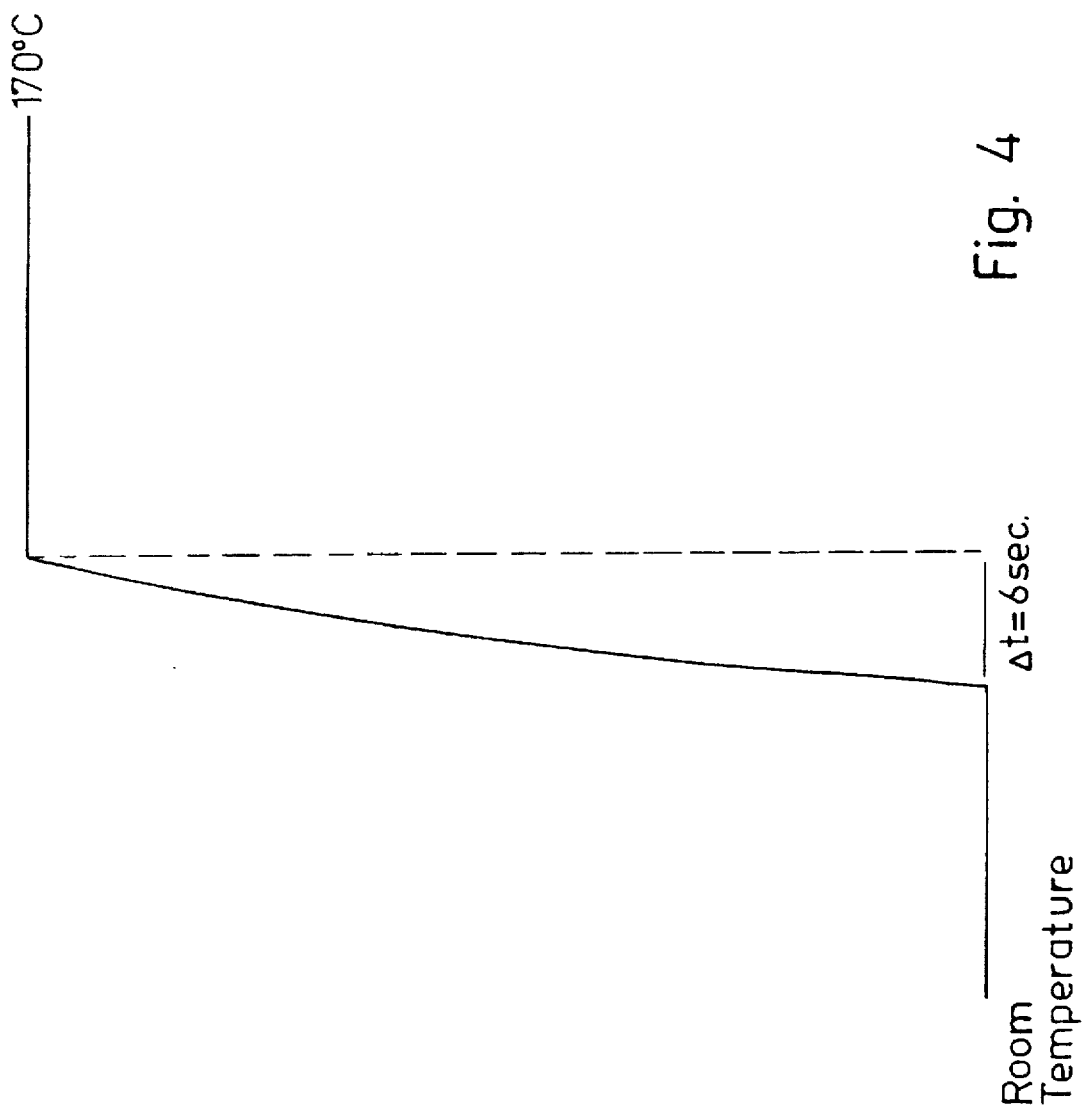
FIG. 4 is the result of heating experiments.

The same probe as in Example 1 was tested for fast heating. Under the same conditions as described with reference to Example 1, the probe was allowed to heat up to 170° C. The result is shown in FIG. 4, from which it can be seen that heating from room temperature to 170° C. was achieved in 6.5 seconds. This result illustrates the effect of the inversion temperature, and proves that heating can be obtained using helium. The experiment was also repeated with a temperature limit of 205° C., and comparable results were obtained, with a heating time of 12 seconds.

All the above description and examples have been provided for the purpose of illustration, and are not intended to limit the invention in any way. Many modifications can be effected in the various parts, shape and construction of the device of the invention. Likewise different gas pairs and gas mixtures can be used, and different low and high temperatures exploited, all without exceeding the scope of the invention.

I claim:

1. A surgical probe having a surface to be brought into contact with cells and/or tissue of a living organism, said surface being capable of being cooled and/or heated and being capable of undergoing fast temperature changes, the fast-changing temperature changing from above room temperature to below about −50° C. and vice versa, and the fast-changing temperature changing from above to below about 0° C. and vice versa at a sub-minute speed, said probe comprising:

a heat exchanger coupled to an orifice, the orifice opening into a jacket;

the jacket being in contact with the surface that is heated and/or cooled, the jacket forming a reservoir capable of housing a fluid in contact with the surface that is heated and/or cooled;

two gas sources providing two gases, a first and a second gas, each of the two gas sources being independently connected to the heat exchanger, the first gas liquifying when expanding through the orifice, the second gas having an inversion temperature lower than a temperature obtained by liquification of the first gas; and means for allowing and stopping a flow of each of the two gases through the orifice.

2. A surgical probe according to claim 1, wherein the surface to be heated and/or cooled is changeable.

3. A surgical probe according to claim 1, wherein the cooling is a cryocooling.

4. A probe according to claim 1, wherein, in operation, in said probe an exhaust gas flows out of the jacket through the heat exchanger to preheat or precool an in-flowing gas from one of said gas sources, and the first gas and the second gas alternatively flow through the heat exchanger and the orifice to cause fast cooling or heating of the surface.

5. A probe according to claim 1, wherein the fast change in temperature is periodic.

6. A probe according to claim 1, wherein the fast change in temperature is controlled and effected at a time selected by an operator.

7. A probe according to claim 1, wherein the first gas is selected from a group consisting essentially of argon, nitrogen, air, krypton, $CF_4$, xenon, and $N_2O$, and the second gas is helium.

8. A probe according to claim 1, wherein the gas sources are pressurized, the pressurized gas sources being gas reservoirs containing gas under pressure.

9. A probe according to claim 1, wherein the gas sources comprise one or more compressors, which draw gas from a reservoir containing gas at a lower pressure than desired.

10. A probe according to claim 1, wherein the heat exchanger is a thin tube or a porous matrix heat exchanger.

11. A probe according to claim 1, wherein, in operation there is generated a fast cyclical change of temperature, comprising sequentially cooling/heating of the surface by alternate gas supply to a Joule-Thomson liquification device comprising a heat-exchanger wherein an incoming gas exchanges heat with an exhaust gas.

12. A method of selectively destroying a plurality of cells and/or tissue of a living organism, comprising:

providing a surgical probe having a surface to be brought into contact with cells and/or tissue of a living organism, said surface being capable of being cooled and/or heated and being capable of undergoing fast temperature changes, the fast-changing temperature changing from above room temperature to below about −50° C. and vice versa, and the fast-changing temperature changing from above to below about 0° C. and vice versa at a sub-minute speed, said probe comprising:

a heat exchanger coupled to an orifice, the orifice opening into a jacket;

the jacket being in contact with the surface that is heated and/or cooled, the jacket forming a reservoir capable of housing a fluid in contact with the surface that is heated and/or cooled;

two gas sources providing two gases, a first and a second gas, each of the two gas sources being independently connected to the heat exchanger, the first gas liquifying when expanding through the orifice, the second gas having an inversion temperature lower than a temperature obtained by liquification of the first gas; and means for allowing and stopping a flow of each of the two gases through the orifice;

contacting the cells to be destroyed with the surface of the probe; and causing extreme temperature changes to take place at the surface of the probe to cool and/or heat the cells in contact with the surface thereby destroying said cells, said extreme temperature changes being from the initial temperature of the surface down to about −190° C. up to about 205° C. or changes between said extreme temperatures of about −190° C. and 205° C.

13. A method according to claim 12, wherein the surface is epidermis.

14. A method according to claim 12, wherein the surface is a human brain.

15. A method according to claim 12, wherein the surface is a human eye.

16. A method according to claim 12, wherein in operation in said probe an exhaust gas flows out of the jacket through the heat exchanger to preheat or precool an in-flowing gas from one of said gas sources and the first gas and the second gas alternatively flow through the heat exchanger and the orifice to cause fast cooling or heating of the surface.

17. A method according to claim 12, wherein in operation in said probe there is generated a fast cyclical change of temperature by sequential cooling/heating of the surface by alternate gas supply to a Joule-Thomson liquification device comprising a heat-exchanger wherein an incoming gas exchanges heat with an exhaust gas.

18. A method according to claim 12, wherein the frequency of the change of temperature is increased by employing less extreme temperatures.

19. A method of accelerating and intensifying cryodestruction of a plurality of cells and/or tissue of a living organism, comprising:

providing a surgical probe having a surface to be brought into contact with cells and/or tissue of a living organism, said surface being capable of being cooled and/or heated and being capable of undergoing fast temperature changes, the fast-changing temperature changing from above room temperature to below about −50° C. and vice versa, and the fast-changing temperature changing from above to below about 0° C. and vice versa at a sub-minute speed, said probe comprising:

a heat exchanger coupled to an orifice, the orifice opening into a jacket;

the jacket being in contact with the surface that is heated and/or cooled, the jacket forming a reservoir capable of housing a fluid in contact with the surface that is heated and/or cooled;

two gas sources providing two gases, a first and a second gas, each of the two gas sources being independently connected to the heat exchanger, the first gas liquifying when expanding through the orifice, the second gas having an inversion temperature lower than a temperature obtained by liquification of the first gas; and means for allowing and stopping a flow of each of the two gases through the orifice;

contacting the cells to be destroyed with the surface of the probe; and causing extreme temperature changes to take place at the surface of the probe to cool and/or heat the cells in contact with the surface thereby destroying said cells, said extreme temperature changes being from the initial temperature of the surface down to about −190° C. up to about 205° C. or changes between said extreme temperatures of about −190° C. and 205° C.

20. A method according to claim 19, wherein the surface is epidermis.

21. A method according to claim 19, wherein the surface is a human brain.

22. A method according to claim 19, wherein the surface is a human eye.

23. A method according to claim 19, wherein in operation in said probe an exhaust gas flows out of the jacket through the heat exchanger to preheat or precool an in-flowing gas from one of said gas sources and the first gas and the second gas alternatively flow through the heat exchanger and the orifice to cause fast cooling or heating of the surface.

24. A method according to claim 19, wherein in operation in said probe there is generated a fast cyclical change of temperature by sequential cooling/heating of the surface by alternate gas supply to a Joule-Thomson liquification device comprising a heat-exchanger wherein an incoming gas exchanges heat with an exhaust gas.

25. A method according to claim 19, wherein the frequency of the change of temperature is increased by employing less extreme temperatures.

26. A probe for industrial, non-medical use for cooling and/or heating another surface other than a human body, said probe having a probe surface to be brought into contact with said other surface, said probe surface being capable of being cooled and/or heated and being capable of undergoing fast temperature changes, the fast-changing temperature changing from above room temperature to below about −50° C. and vice versa, and the fast-changing temperature changing from above to below about 0° C. and vice versa at a sub-minute speed, said probe comprising:

a heat exchanger coupled to an orifice, the orifice opening into a jacket;

the jacket being in contact with the probe surface that is heated and/or cooled, the jacket forming a reservoir capable of housing a fluid in contact with the probe surface that is heated and/or cooled;

two gas sources providing two gases, a first and a second gas, each of the two gas sources being independently connected to the heat exchanger, the first gas liquifying when expanding through the orifice, the second gas having an inversion temperature lower than a temperature obtained by liquification of the first gas; and means for allowing and stopping a flow of each of the two gases through the orifice.

27. A probe according to claim 26, wherein, in operation, in said probe an exhaust gas flows out of the jacket through the heat exchanger to preheat or precool an in-flowing gas from one of said gas sources, and the first gas and the second gas alternatively flow through the heat exchanger and the orifice to cause fast cooling or heating of the probe surface.

28. A probe according to claim 26, wherein the fast change in temperature is periodic.

29. A probe according to claim 26, wherein the fast change in temperature is controlled and effected at a time selected by an operator.

30. A probe according to claim 26, wherein the first gas is selected from a group consisting essentially of argon, nitrogen, air, krypton, $CF_4$, xenon, and $N_2O$, and the second gas is helium.

31. A probe according to claim 26, wherein the gas sources are pressurized, the pressurized gas sources being gas reservoirs containing gas under pressure.

32. A probe according to claim 26, wherein the gas sources comprise one or more compressors, which draw gas from a reservoir containing gas at a lower pressure than desired.

33. A probe according to claim 26, wherein the heat exchanger is a thin tube or a porous matrix heat exchanger.

34. A probe according to claim 26, wherein, in operation there is generated a fast cyclical change of temperature, comprising sequentially cooling/heating of the probe surface by alternate gas supply to a Joule-Thomson liquification device comprising a heat-exchanger wherein an incoming gas exchanges heat with an exhaust gas.

35. A probe according to claim 26, wherein the cooling is a cryo-cooling.

36. A probe according to claim 26, wherein the probe surface to be heated and/or cooled is changeable.

* * * * *